United States Patent
Yokoi

(10) Patent No.: US 12,053,321 B2
(45) Date of Patent: Aug. 6, 2024

(54) PHANTOM, RADIOGRAPHIC IMAGING DEVICE, AND CALIBRATION METHOD FOR PHOTON COUNTING DETECTOR

(71) Applicant: FUJIFILM Healthcare Corporation, Kashiwa (JP)

(72) Inventor: Kazuma Yokoi, Kashiwa (JP)

(73) Assignee: FUIIFILM Healthcare Corporation, Chiba (JP)

( * ) Notice: Subject to any disclaimer, the term of this patent is extended or adjusted under 35 U.S.C. 154(b) by 141 days.

(21) Appl. No.: 17/830,633

(22) Filed: Jun. 2, 2022

(65) Prior Publication Data

US 2022/0395248 A1   Dec. 15, 2022

(30) Foreign Application Priority Data

Jun. 14, 2021  (JP) ................................. 2021-098571

(51) Int. Cl.
*A61B 6/58* (2024.01)
*A61B 6/42* (2024.01)
*G01T 7/00* (2006.01)

(52) U.S. Cl.
CPC ............ *A61B 6/583* (2013.01); *A61B 6/4241* (2013.01); *A61B 6/585* (2013.01); *G01T 7/005* (2013.01)

(58) Field of Classification Search
CPC ....... A61B 6/583; A61B 6/4241; A61B 6/585; A61B 6/4405; A61B 6/032; A61B 6/035; A61B 6/44; A61B 6/481; A61B 6/504
See application file for complete search history.

(56) References Cited

U.S. PATENT DOCUMENTS

| | | | |
|---|---|---|---|
| 2005/0078802 A1* | 4/2005 | Lang ...................... | A61B 6/583 378/207 |
| 2014/0233693 A1* | 8/2014 | Wang ..................... | A61B 6/582 378/207 |

(Continued)

FOREIGN PATENT DOCUMENTS

| | | |
|---|---|---|
| JP | 2008-509737 A | 4/2008 |
| JP | 2015-204985 A | 11/2015 |
| WO | WO 2006-033712 A | 3/2006 |

OTHER PUBLICATIONS

Taly Gilat Schmidt, et al., "A Spectral CT method to directly estimate basis material maps from experimental photon-counting data", IEEE Transactions on Medical Imaging, vol. 36, No. 6, pp. 1808-1819, Sep. 2017.

(Continued)

*Primary Examiner* — David P Porta
*Assistant Examiner* — Casey Bryant
(74) *Attorney, Agent, or Firm* — Paul Teng

(57) ABSTRACT

There are provided a phantom capable of reducing the time required to acquire calibration data even if a radiation field is large, a radiographic imaging device, and a method for calibrating a photon counting detector. A phantom, which is used in acquisition of calibration data for a photon counting detector that outputs an electric signal based on photon energy of incident radiation, includes a first basis material and a second basis material that are known materials. The first basis material has a smaller attenuation coefficient for the radiation than that of the second basis material. The first basis material varies in thickness in a stepwise fashion in a direction perpendicular to a radiation field of the radiation and, in each step, the step decreases in thickness with (Continued)

distance from a center of the radiation field in a direction of arrangement of detection elements of the photon counting detector.

13 Claims, 12 Drawing Sheets

(56) References Cited

U.S. PATENT DOCUMENTS

| | | | |
|---|---|---|---|
| 2015/0301202 A1* | 10/2015 | Takagi | A61B 6/032 378/207 |
| 2016/0113603 A1 | 4/2016 | Schirra et al. | |
| 2022/0395248 A1* | 12/2022 | Yokoi | A61B 6/583 |

OTHER PUBLICATIONS

Japanese official action dated Nov. 14, 2023 (and machine translation thereof) in connection with Japanese Patent Application No. 2021-098571.

* cited by examiner

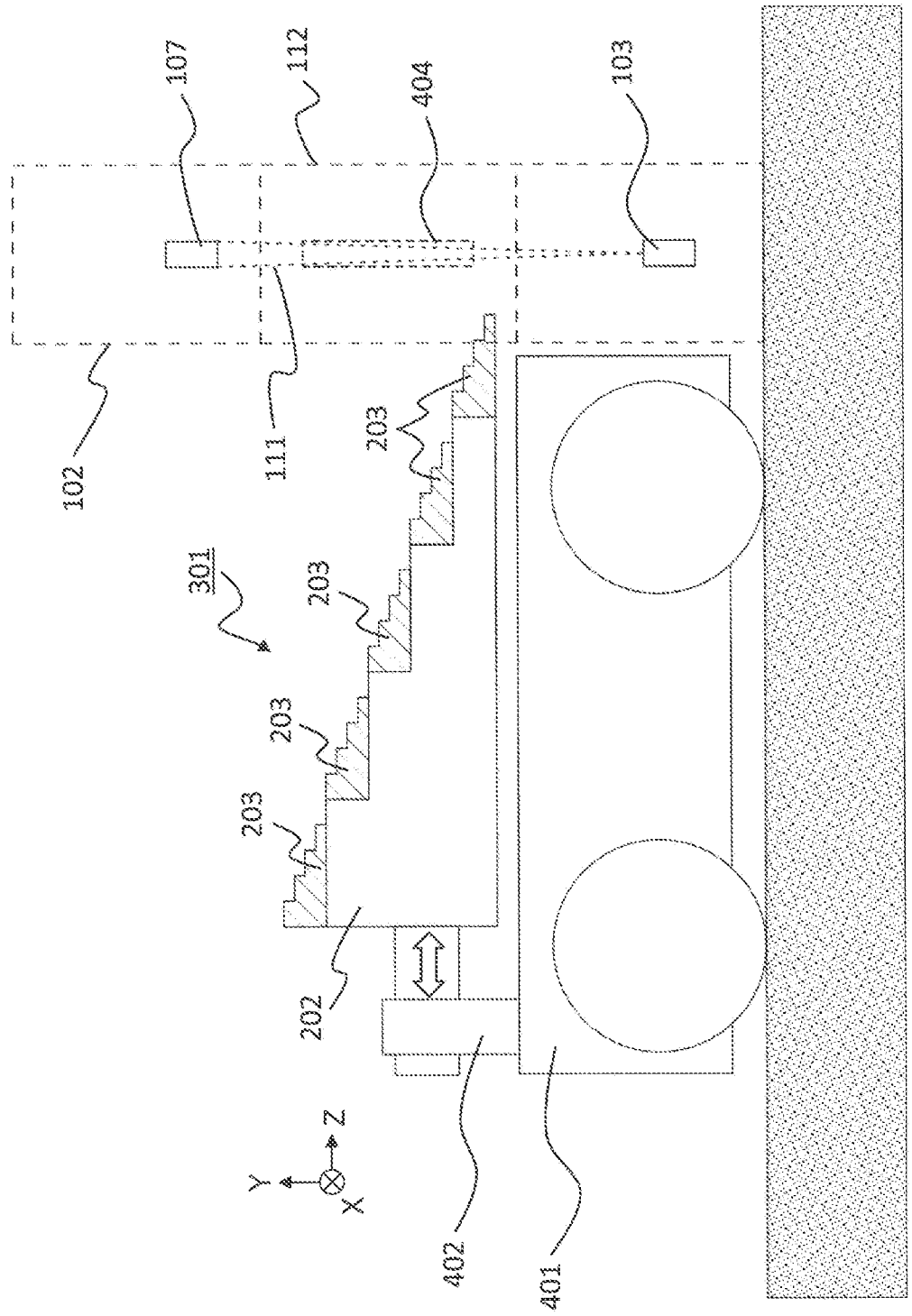

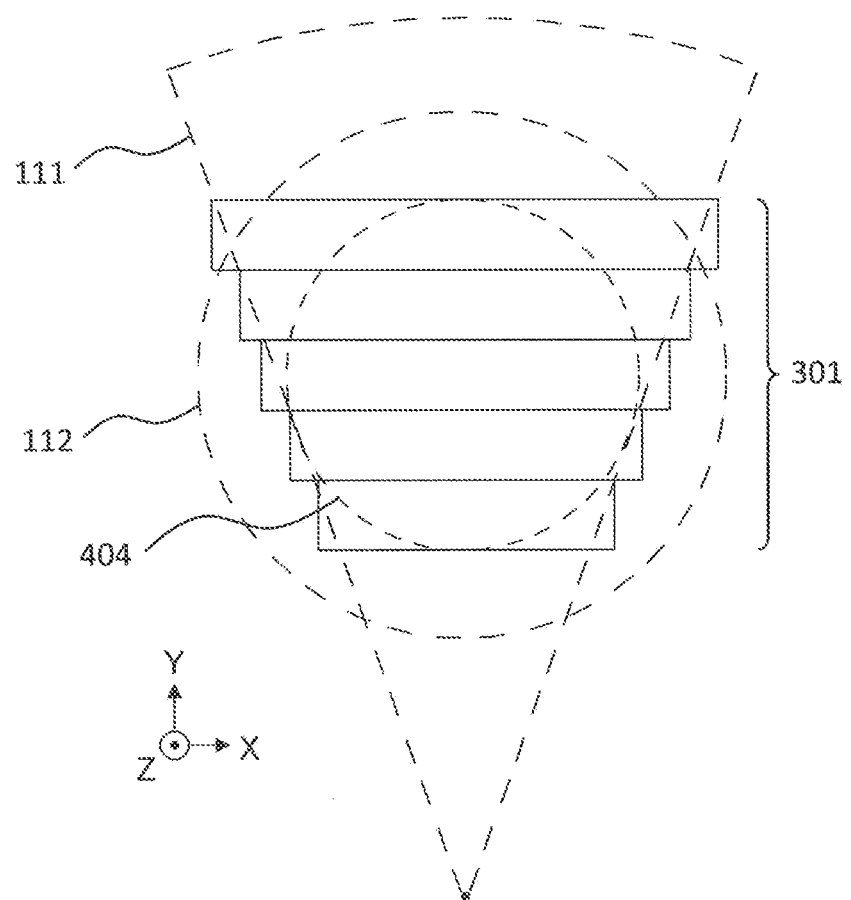

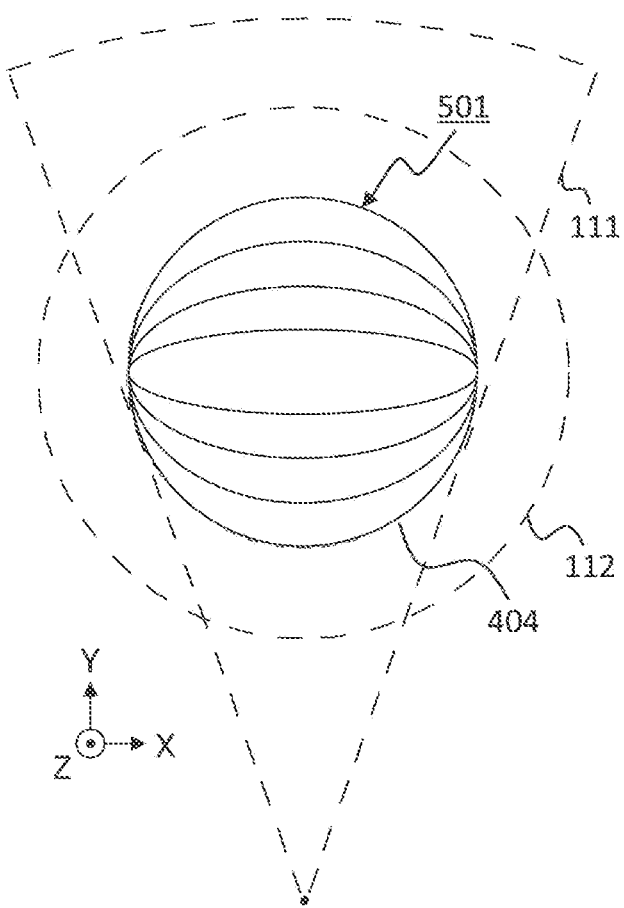

PHANTOM, RADIOGRAPHIC IMAGING DEVICE, AND CALIBRATION METHOD FOR PHOTON COUNTING DETECTOR

CLAIM OF PRIORITY

The present application claims priority from Japanese Patent Application JP 2021-098571 filed on Jun. 14, 2021, the content of which is hereby incorporated by reference into this application.

BACKGROUND OF THE INVENTION

The present invention relates to a radiographic imaging device including a photon counting detector and, more particularly to a phantom used in calibration of the photon counting detector.

A PCCT (Photon Counting Computed Tomography) apparatus including a photon counting detector which is a detector adopting a photon counting scheme is under development. Because the photon counting detector is capable of measuring photon energy which is energy of incident radiation photons, the PCCT apparatus provides medical images in which materials of different compositions are discriminated, e.g., medical images in which an iodinated contrast agent used in angiography is discriminated from calcified plaque in blood vessels. For obtaining a medical image in which materials are discriminated, the relationship between photon energy and output when a phantom is measured by the photon counting detector is required to be pre-acquired as calibration data for each detector element, the phantom being composed of a combination of a plurality of basis materials of which composition and thickness are known.

For example, "A Spectral CT method to directly estimate basis material maps from experimental photon-counting data", in IEEE Transactions on Medical Imaging, vol. 36, no. 6, pp. 1808-1819, September 2017 by Taly Gilat Schmidt et al. discloses acquisition of 25 items of calibration data using a stepped phantom composed of zero to four flat acrylic plates each of 2.54 cm in thickness and zero to four flat aluminum plates each of 0.635 cm in thickness.

The above reference, however, merely discloses the phantom used in a small radiation field on the order of 13 cm. If the stepped phantom according to the above reference is extended to cover a large radiation field on the order of 50 cm, this results in a phantom having an unmanageable weight, and therefore a long time is required to acquire the calibration data for the photon counting detector.

SUMMARY OF THE INVENTION

It is accordingly an object of the present invention to provide a phantom capable of reducing the time required to acquire calibration data even if a radiation field is large, a radiographic imaging device, and a method for calibrating a photon counting detector.

To achieve the above objection, an aspect of the present invention provides a phantom used in acquisition of calibration data for a photon counting detector that outputs an electric signal based on photon energy of incident radiation. The phantom includes a first basis material and a second basis material that are known materials. The first basis material has a smaller attenuation coefficient for the radiation than that of the second basis material. The first basis material varies in thickness in a stepwise fashion in a direction perpendicular to a radiation field of the radiation and, in each step, the step decreases in thickness with distance from a center of the radiation field in a direction of arrangement of detection elements of the photon counting detector.

Another aspect of the present invention provides a radiographic imaging device including: a photon counting detector that outputs an electric signal based on photon energy of incident radiation; and a storage for storing calibration data acquired using the above-described phantom.

Further another aspect of the present invention provides a method for calibrating a photon counting detector that outputs an electric signal based on photon energy of incident radiation. The method includes the step of acquiring calibration data for the photon counting detector by using a phantom. The phantom includes a first basis material and a second basis material that are known materials, and the first basis material has a smaller attenuation coefficient for the radiation than that of the second basis material. The first basis material varies in thickness in a stepwise fashion in a direction perpendicular to a radiation field of the radiation and, in each step, the step decreases in thickness with distance from a center of the radiation field in a direction of arrangement of detection elements of the photon counting detector.

According to the present invention, it is possible to provide a phantom capable of reducing the time required to acquire calibration data even if a radiation field is large, a radiographic imaging device, and a method for calibrating a photon counting detector.

BRIEF DESCRIPTION OF THE DRAWINGS

FIG. 3 is a diagram illustrating a conventional stepped phantom;

FIG. 4 is a diagram illustrating the relationship between a conventional stepped phantom and an opening of a gantry;

FIG. 5C is a diagram illustrating the relationship between an opening of a gantry and the coupled elliptic phantom in the first embodiment;

DETAILED DESCRIPTION OF THE PREFERRED EMBODIMENTS

Embodiments according to the present invention will now be described with reference to the accompanying drawings. The present invention is applied to a radiographic imaging device including a radiation source and a photon counting detector. The following description provides an example where radiation is X-rays and the radiographic imaging device is an X-ray CT apparatus.

First Embodiment

Figure 1:
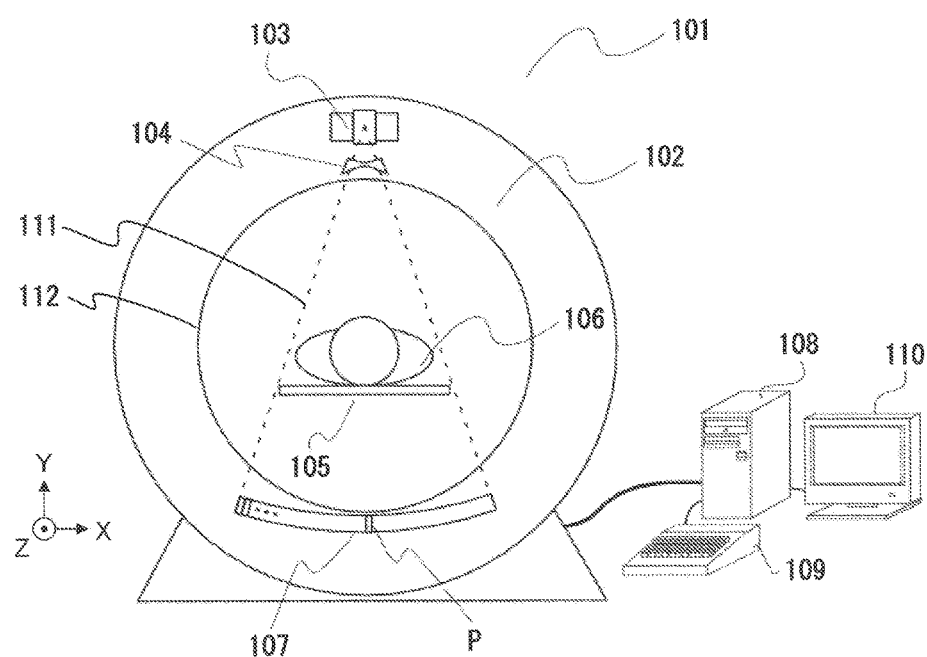
FIG. 1 is a diagram illustrating an overall configuration of a PCCT apparatus.

FIG. 1 is a diagram illustrating an overall configuration of an X-ray CT apparatus 101 in a first embodiment according to the present invention. In the drawings, the direction of the short side of the paper is defined as an X axis, the direction of the long side is defined as a Y axis, and a direction orthogonal to the XY plane is defined as a Z axis. The X-ray CT apparatus 101 includes a gantry 102, an X-ray tube 103, a bowtie filter 104, a bed 105, a detector panel 107, an arithmetic apparatus 108, an input apparatus 109, and a display apparatus 110.

An object 106 under examination is laid on the bed 105, and placed within an opening 112 installed in the gantry 102. X-rays 111, which are emitted from the X-ray tube 103, are formed into a beam shape suitable for a size of the object 106 under examination by the bowtie filter 104 to be applied to the object 106 under examination, which is then detected by the detector panel 107 after passing through the object 106 under examination. The X-ray tube 103 and the detector panel 107 are attached to the gantry 102 to face each other on the opposite sides of the object 106 under examination, so that the X-ray tube 103 and the detector panel 107 are rotated around the object 106 under examination by a rotation drive of the gantry 102. The X-ray irradiation from the X-ray tube 103 and the X-ray measurement by the detector panel 107 are repeated with rotation of the X-ray tube 103 and the detector panel 107, thereby acquiring projection data at various angles of projection.

The arithmetic apparatus 108 performs the image reconstruction processing on the acquired projection data in order to generate a tomographic image of the object 106 under examination, and the tomographic image is displayed on the display apparatus 110. Also, when the projection data is acquired during a relative movement in the Z axis direction between the gantry 102 and the bed 105 on which the object 106 under examination lies, a volume image of the object 106 under examination is generated. It is noted that the amount of X rays emitted from the X-ray tube 103, the rotational speed of the gantry 102, and the speed of relative movement between the gantry 102 and the bed 105 are set based on scanning conditions input through the input apparatus 109 by the operator. The arithmetic apparatus 108 has a similar hardware configuration to that of typical computer apparatus, and includes a CPU (Central Processing Unit), memory, an HDD (Hard Disk Drive) and the like so that the arithmetic apparatus 108 performs correction processing on projection data and the like, and control on all parts.

The detector panel 107 is configured by arranging a plurality of detection elements P in an arc shape centered around the X-ray focal point of the X-ray tube 103. Each detection element P is a photon counting detector to measure photon energy which is energy of the incident X-ray photons, and provides output based on the photon energy.

The X-ray CT apparatus 101 including the photon counting detectors may acquire a photon energy spectrum related to the projection data of the object 106 under examination, and thus generate a medical image in which materials of different compositions are discriminated and a medical image in which the materials are separated into a plurality of energy components. It is noted that, for obtaining a medical image in which materials of different compositions are discriminated and the like, the relationship between output and photon energy when a combination of a plurality of basis materials of known composition and known thickness is measured by the photon counting detectors is required to be pre-calibrated for each detector element.

Figure 2:
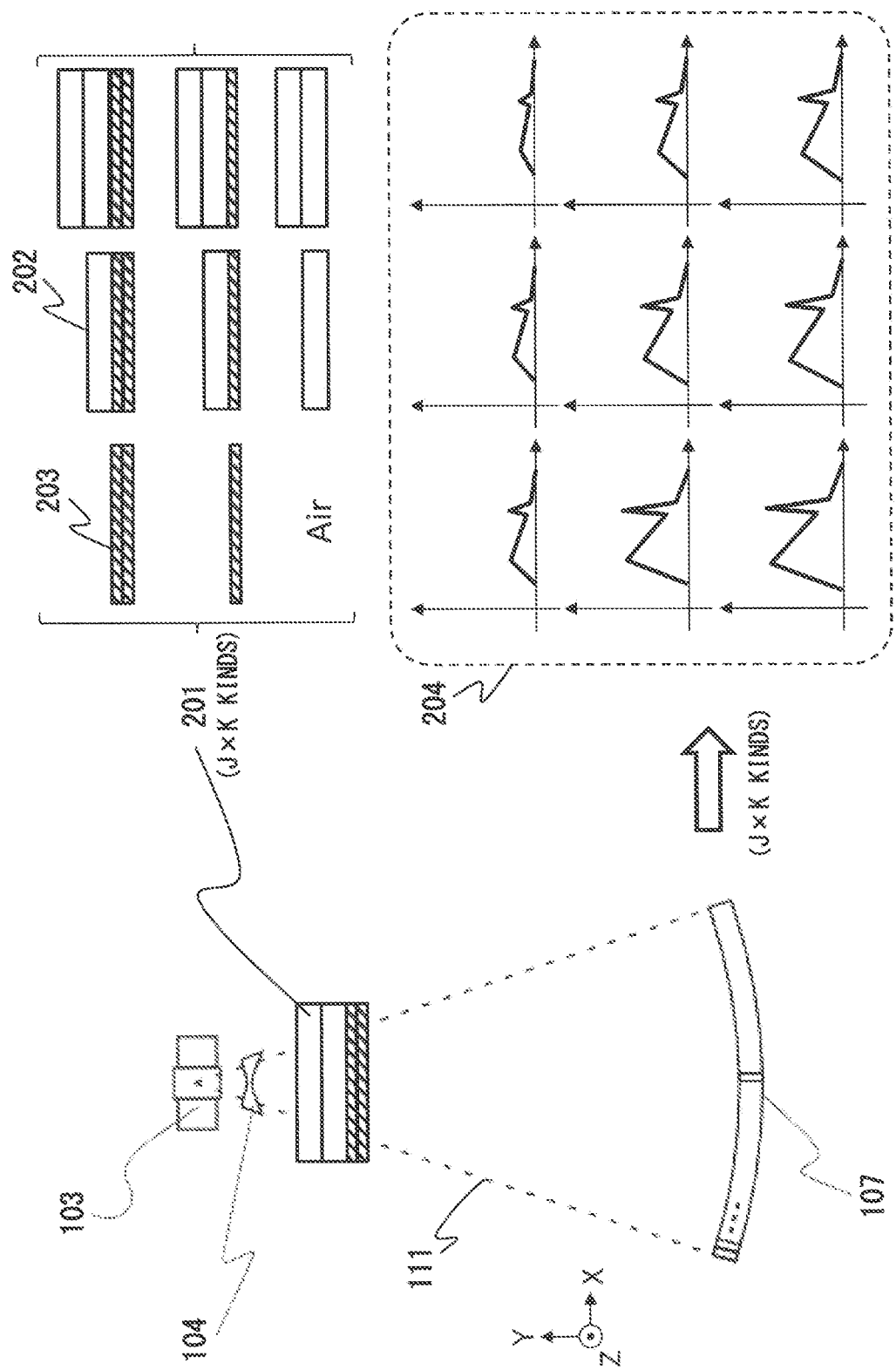
FIG. 2 is a diagram illustrating calibration of a photon counting detector.

With reference to FIG. 2, the calibration of the photon counting detector is described. The photon counting detector is calibrated by using a combination 201 of a plurality of basis materials of known composition and known thickness, for example, the combination 201 of two basis materials, a first basis material 202 and a second basis material 203. For the basis material combination 201, a plurality of plates of different thicknesses may be used for each basis material. For example, if J kinds of the first basis materials 202 differ in thickness and K kinds of the second basis materials 203 differ in thickness, J×K kinds of basis material combinations 201 are used and, with respect to each combination, a photon energy spectrum is acquired by each detector element. In FIG. 2, if J=3 and K=3, nine photon energy spectra are shown as calibration data 204. The acquired calibration data 204 is stored in a storage of the arithmetic apparatus 108 for use in calibration of projection data of the object 106 under examination.

With reference to FIG. 3, a conventional stepped phantom 301 is described, which is illustrated by example in "A Spectral CT method to directly estimate basis material maps from experimental photon-counting data" by Taly Gilat Schmidt et al. mentioned in "Description in the Related Art". The stepped phantom 301 includes the first basis material 202 and the second basis material 203, in which the first basis material 202 is formed by using acrylic and the second basis material 203 is formed by using aluminum with an X-ray attenuation coefficient greater than that of acrylic. Also, the first basis material 202 has four steps of a stairway formed thereon, and the second basis materials 203 each having four steps of a stairway are placed on the respective steps of the first basis material 202. Specifically, 25 kinds of basis material combinations are formed by the stepped phantom 301 in which the first basis material 202 and the second basis materials 203 each of which has five thicknesses including a thickness of zero are arranged in the Z axis direction. For allowing the X rays 111 entering the detector panel 107 to pass through the basis materials of the same thickness, a Z-axial length of each step of each second basis material 203 is set longer than the Z-axial length of the X rays 111 entering the detector panel 107.

The stepped phantom 301 is mounted to a carriage 401 through a drive unit 402, and is moved in the Z axis direction by the drive unit 402. The stepped phantom 301 is moved in the Z axis direction in order to position a predetermined basis material combination within a radiation field 404 of the X rays 111. For generating a typical tomographic image of an object under examination, the radiation field 404 has a diameter on the order of 50 cm, and therefor the first basis material 202 is also required to have a maximum thickness nearly equal to that. The second basis material 203 is required to have a thickness sufficient to attenuate X rays to a similar level to that of the first basis material 202 with the maximum thickness. The stepped phantom 301 including the first basis material 202 with a maximum thickness on the order of 50 cm has a weight over 100 Kg, which is difficult to be handled, and therefore a long time is required to acquire the calibration data.

With reference to FIG. 4, the relationship between the stepped phantom 301 and the opening 112 of the gantry 102 is described. If the stepped phantom 301 is extended to cover the radiation field 404, the stepped phantom 301 has a larger size than the opening 112 so that it cannot pass through the opening 112. In other words, the stepped phantom 301 is difficult to be handled in terms of size as well as weight. To address this, in the first embodiment according to the present invention, a phantom is reduced in weight and/or size in order to shorten the time required to acquire calibration data.

Figure 5A:
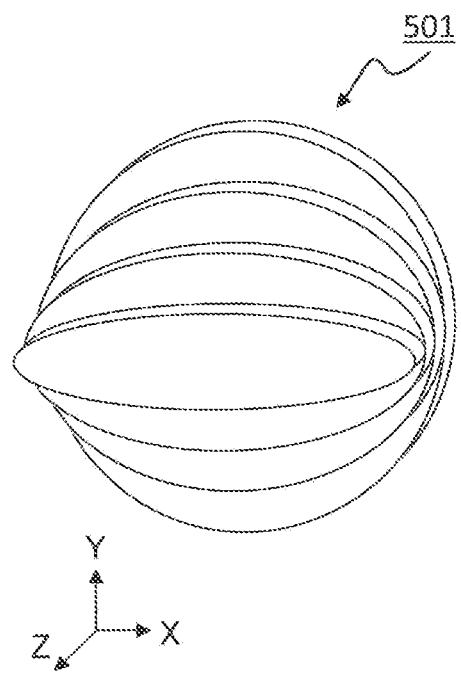
FIG. 5A is a perspective view illustrating a coupled elliptic phantom in a first embodiment according to the present invention.
Figure 5B:
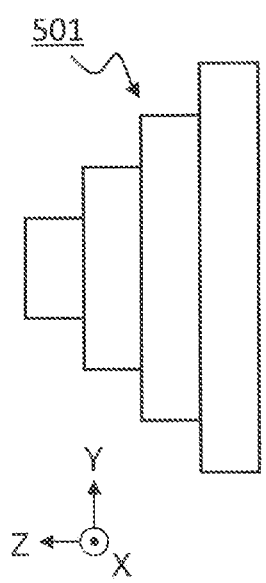
FIG. 5B is a side view illustrating the coupled elliptic phantom in the first embodiment.

With reference to FIGS. 5A to 5C, a coupled elliptic phantom 501 is described which is a phantom in the first embodiment according to the present invention. FIG. 5A is a perspective view of a coupled elliptic phantom 501, FIG. 5B is a side view thereof, and FIG. 5C is a front view thereof, which are diagrams illustrating the relationship between the opening 112 and the coupled elliptic phantom 501.

The coupled elliptic phantom 501 is formed of the first basis material 202 with an X-ray attenuation coefficient less than that of the second basis material 203, and varies in thickness in a stepwise fashion in a direction perpendicular to the radiation field 404, i.e., in the Z axis direction. Also, in each step of the coupled elliptic phantom 501 in the Z axis direction, the step decreases in thickness with distance from the center of the radiation field 404 in the direction of arrangement of the detection elements P of the detector panel 107.

More specifically, the coupled elliptic phantom 501 is formed by coupling together in the Z axis direction a plurality of elliptic cylinders which are identical in length of the major axis and vary in length of the minor axis. It is noted that one of the plurality of elliptic cylinders has preferably a major axis and a minor axis that are equal in length to each other. As illustrated in FIG. 5C, the coupled elliptic phantom 501 has a size fitting into the radiation field 404. Therefore, the coupled elliptic phantom 501 does not have an unmanageable weight and the time required to acquire calibration data may be shortened. Further, because an elliptic cylinder is similar in shape to the object 106 under examination, the calibration data includes influences of scattered radiation produced by the object 106 under examination.

It is noted that where N is the number of elliptic cylinders, i.e., the number of steps in the Z axis direction, the length of the minor axis of an i-th elliptic cylinder from one end of the Z axis direction is preferably i/N times the length of the major axis thereof. Because the minor axis and the major axis of the i-th elliptic cylinder are at a ratio of i to N, a difference in X-ray transmission length is approximately equal between neighboring elliptic cylinders in the Z axis direction, so that handling the acquired calibration data is facilitated.

Figure 6:
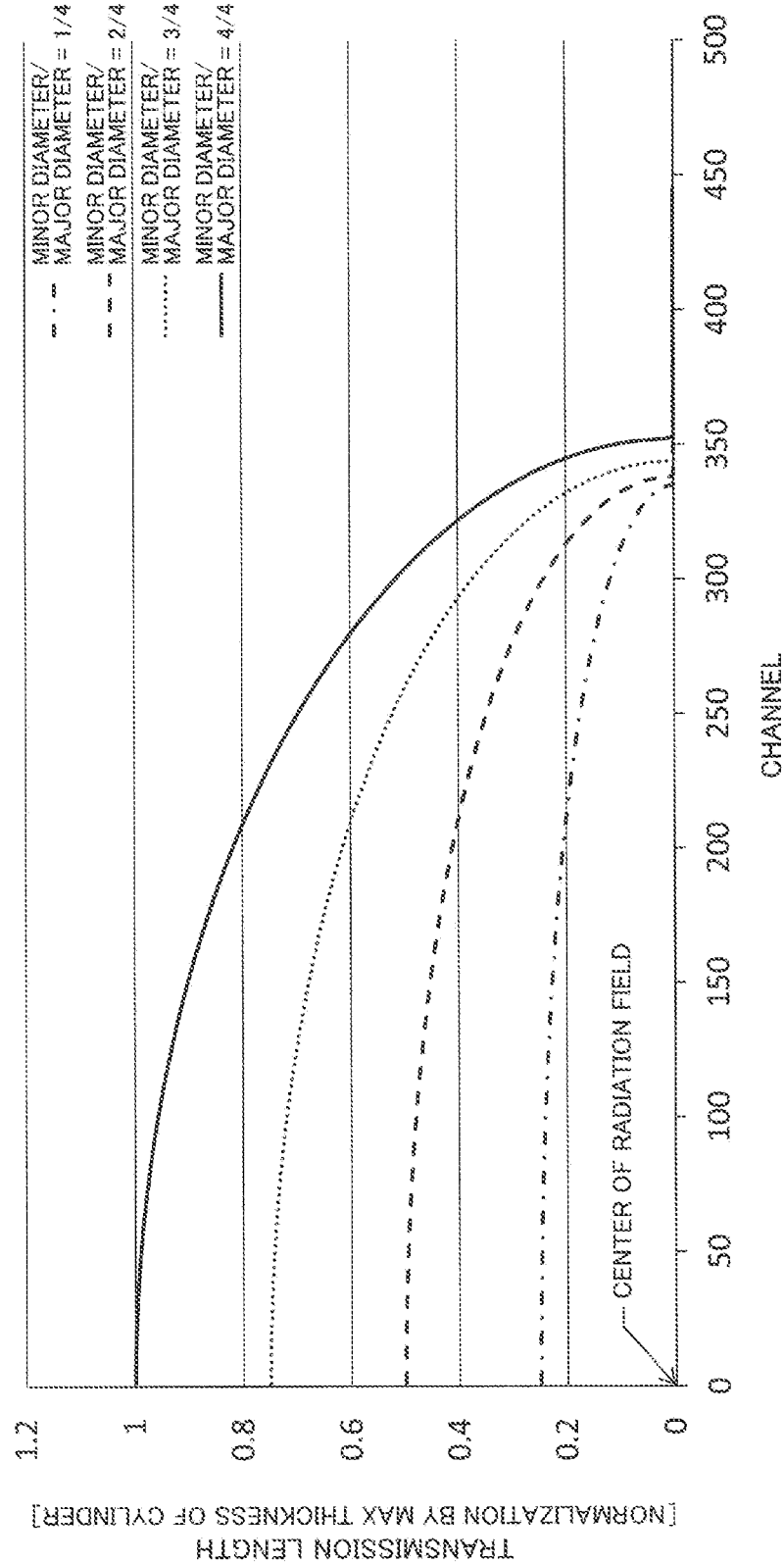
FIG. 6 is a graph showing transmission lengths of the coupled elliptic phantom for each channel in the first embodiment.

FIG. 6 is an example graph showing X-ray transmission lengths of the coupled elliptic phantom 501 in each channel of the detector panel 107. In the graph illustrated in FIG. 6, the vertical axis represents normalized X-ray transmission lengths and the horizontal axis represents channels of the detector panel 107. It is noted that the coupled elliptic phantom 501 is formed by coupling the four elliptic cylinders together. The ratio between the minor diameter and the major diameter of each elliptic cylinder is 1:4, 2:4, 3:4, 4:4. Because of the left-right symmetry of the detector panel 107, the left end of the horizontal axis is aligned with the center of the radiation field 404, and the vertical axis is normalized by a diameter which is a maximum thickness of a cylinder with a minor diameter and a major diameter in a 4-to-4 ratio. As illustrated in FIG. 6, a difference in X-ray transmission length between neighboring elliptic cylinders in the Z axis direction is approximately equal in most channels of the detector panel 107, and therefore this makes it easy to handle the calibration data acquired using the coupled elliptic phantom 501.

As described above, the weight of the coupled elliptic phantom 501 in the first embodiment is not unmanageable, making it possible to shorten the time to acquire the calibration data. Also, if the length of the minor axis of an i-th elliptic cylinder from one end of the Z axis direction is i/N times the length of the major axis thereof, the acquired calibration data is easily handled. It is noted that the calibration data acquired using the coupled elliptic phantom 501 is stored in the storage of the arithmetic apparatus 108 and used for calibration of the projection data of the object 106 under examination.

Second Embodiment

In the first embodiment, the coupled elliptic phantom 501 formed by coupling a plurality of elliptic cylinders together in the Z axis direction has been described. A description in a second embodiment is given of a coupled component phantom that is formed by coupling, together in the Z axis direction, components each having a thickness equal to the X-ray transmission length allocated thereto in the radiation field 404, i.e., a thickness obtained by multiplying it by a coefficient equal to or less than one.

As in the case of the coupled elliptic phantom 501, the coupled component phantom is formed of the first basis material 202, and varies in thickness in a stepwise fashion in a direction perpendicular to the radiation field 404, i.e., in the Z axis direction. Also, in each step of the coupled component phantom in the Z axis direction, the step decreases in thickness with distance from the center of the radiation field 404 in the direction of arrangement of the detection elements P of the detector panel 107.

Figure 7A:
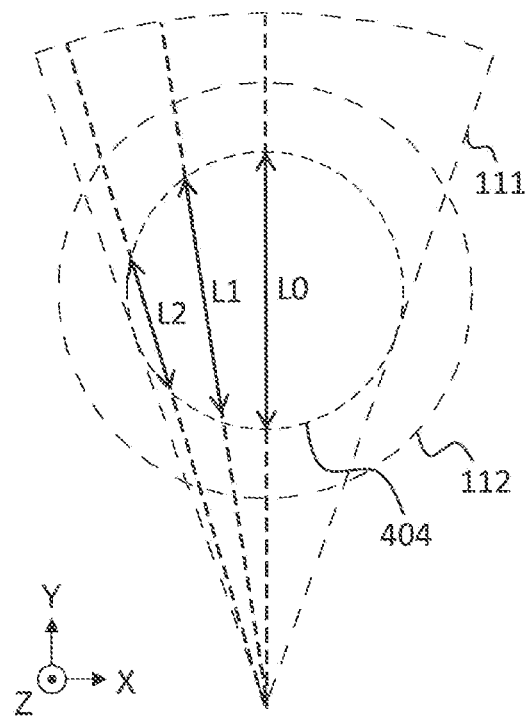
FIG. 7A is a diagram illustrating X-ray transmission lengths in a radiation field.
Figure 7B:
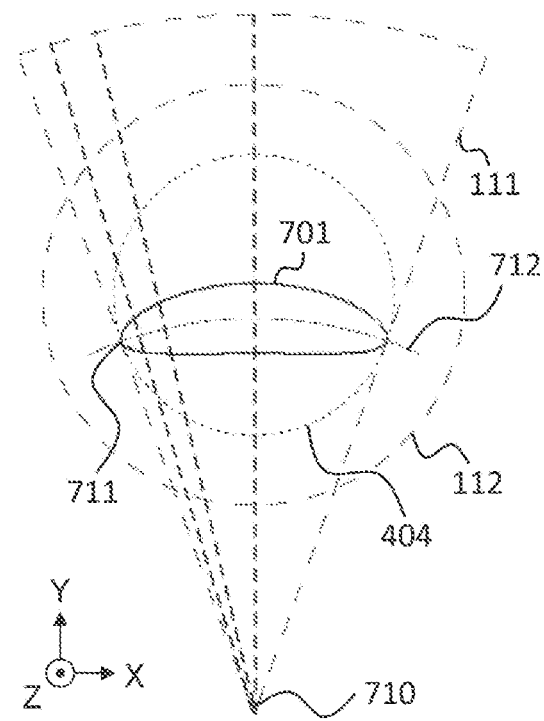
FIG. 7B is a diagram illustrating a first component in a second embodiment according to the present invention.
Figure 7C:
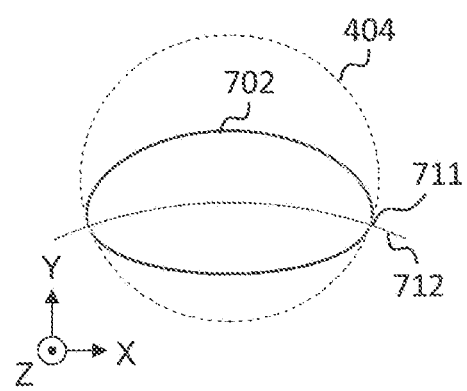
FIG. 7C is a diagram illustrating a second component in the second embodiment.
Figure 7D:
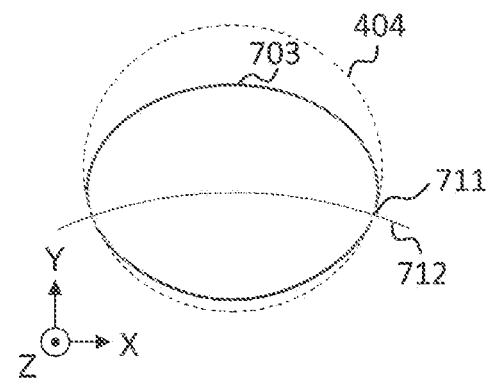
FIG. 7D is a diagram illustrating a third component in the second embodiment.

With reference to FIGS. 7A to 7D, the coupled component phantom is described. FIG. 7A is a diagram illustrating the X-ray transmission length in the radiation field 404, and FIGS. 7B, 7C, and 7D are diagrams respectively illustrating a first component 701, a second component 702, and a third component 703 that are parts of the coupled component phantom.

As illustrated in FIG. 7A, the X-ray transmission length in the radiation field 404 varies for each detection element of the detector panel 107. An X-ray transmission length L0 passing through the center of the radiation field 404 is the longest, and the X-ray transmission length becomes shorter with distance from the center, such as L1, L2. Each of the first component 701, the second component 702, and the third component 703, as illustrated in FIGS. 7B to 7D, has a thickness obtained by multiplying the X-ray transmission length in the radiation field 404 by a coefficient equal to or less than one. That is, as in the case of the coupled elliptic phantom 501, the coupled component phantom has a size fitting into the radiation field 404, and thus does not have an unmanageable weight, and the time required to acquire calibration data can be shortened. Further, because each component is similar in shape to the object 106 under examination, the calibration data includes influences of scattered radiation produced by the object 106 under examination.

It is noted that where N is the number of components, i.e., the number of steps in the Z axis direction, the X-ray transmission length of an i-th component from one end of the Z axis direction is preferably i/N times the X-ray transmission length in the radiation field 404. For example, of the four components, in the first component 701 an X-ray transmission length is set at ¼ times the radiation field 404, in the second component 702 an X-ray transmission length is set at 2/4 times and in the third component 703 an X-ray transmission length is set at ¾ times. Because a ratio between the X-ray transmission length of the i-th component and the X-ray transmission length in the radiation field 404 is of i to N, a difference in X-ray transmission length between neighboring components in the Z axis direction is equal among all channels of the detector panel 107, so that handling the acquired calibration data is facilitated.

Also, the X-ray transmission length of each component is preferably set with respect to an arc 712 that is centered around an X-ray focal point 710 and passes through a contact point 711 between the radiation field 404 and a tangent to the radiation field 404 passing through the X-ray focal point 710. More specifically, one half of the X-ray transmission length of each component is preferably set on each of the focal point 710 side and the other sides of the arc 712. Setting the X-ray transmission length of each component with respect to the arc 712 makes it possible to align the channels on which the X-ray transmission lengths of the respective components become zero.

Figure 8:
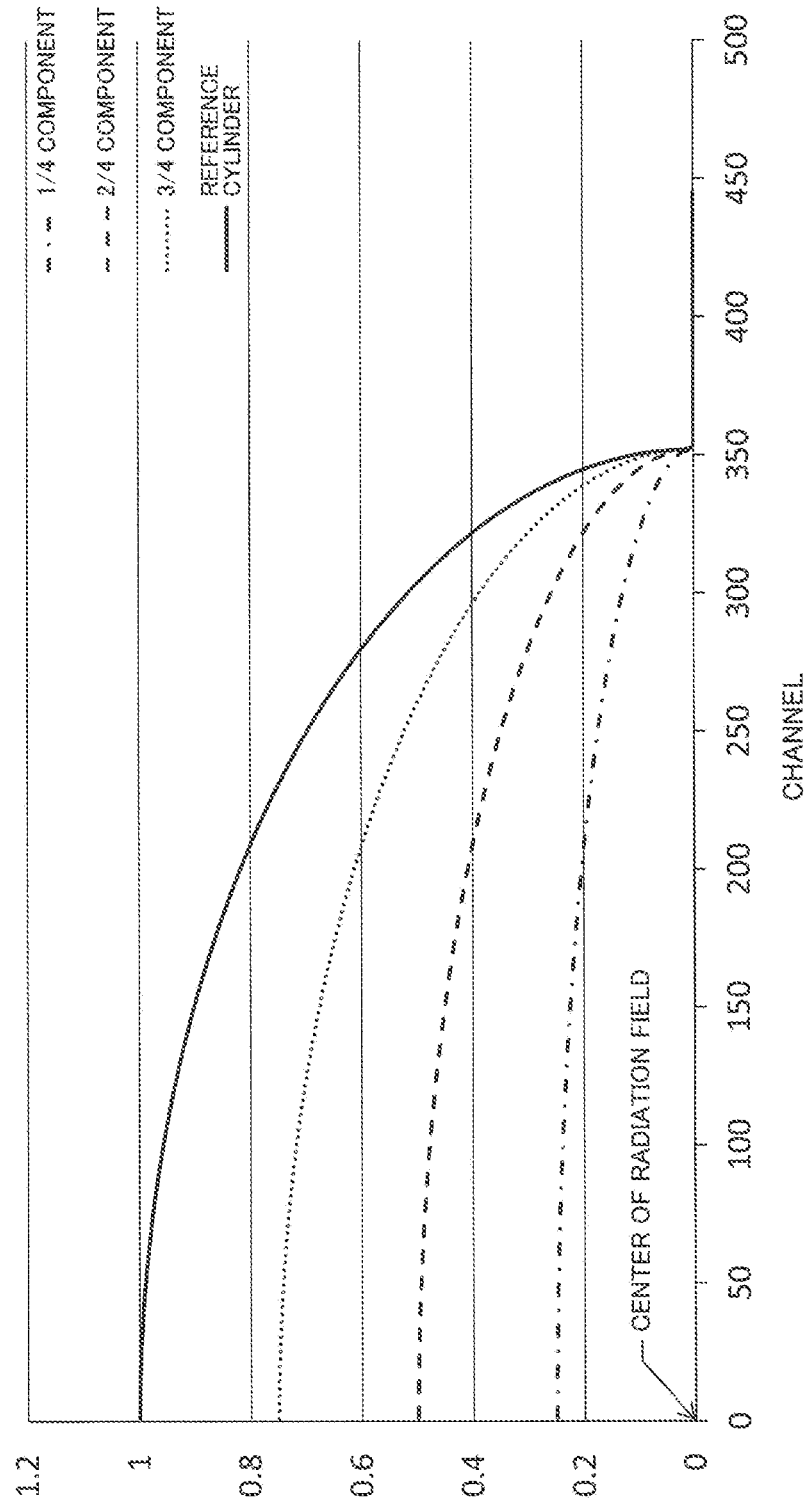
FIG. 8 is a graph showing transmission lengths of the coupled component phantom for each channel in the second embodiment.

FIG. 8 is an example graph showing the X-ray transmission lengths of the coupled component phantom on the respective channels of the detector panel 107. As in the case of FIG. 6, in the example graph illustrated in FIG. 8, the vertical axis represents normalized X-ray transmission lengths and the horizontal axis represents the channels of the detector panel 107. It is noted that the coupled component phantom is formed by coupling the first component 701, the second component 702, and the third component 703 to a cylinder. The X-ray transmission length of each component is ¼ times, 2/4 times, ¾ times the X-ray transmission length of the cylinder having an outer diameter equal to the diameter of the radiation field 404. Because of the left-right symmetry of the detector panel 107, the left end of the horizontal axis is aligned with the center of the radiation field 404, and the vertical axis is normalized by the diameter which is a maximum thickness of the cylinder. As illustrated in FIG. 8, a difference in X-ray transmission length between neighboring components in the Z axis direction is equal among most channels of the detector panel 107, so that the channels on which the X-ray transmission lengths become zero can be aligned. As a result, handling the calibration data acquired using the coupled component phantom may be facilitated.

As described above, the coupled component phantom in the second embodiment does not have an unmanageable weight, and therefore the time to acquire the calibration data can be shortened. Also, if the X-ray transmission length of an i-th component from one end of the Z axis direction is i/N times the X-ray transmission length of the radiation field 404, the acquired calibration data is easily handled. It is noted that the calibration data acquired using the coupled component phantom is stored in the storage of the arithmetic apparatus 108 and used for calibration of the projection data of the object 106 under examination.

The coupled elliptic phantom 501 in the first embodiment and the coupled component phantom in the second embodiment are each formed of the first basis material 202, and therefore combined with a second basis material phantom formed of the second basis material 203 to be used to acquire the calibration data. When the first basis material 202 and the second basis material 203 are combined together to be used, both of them are preferably driven individually.

Figure 9:
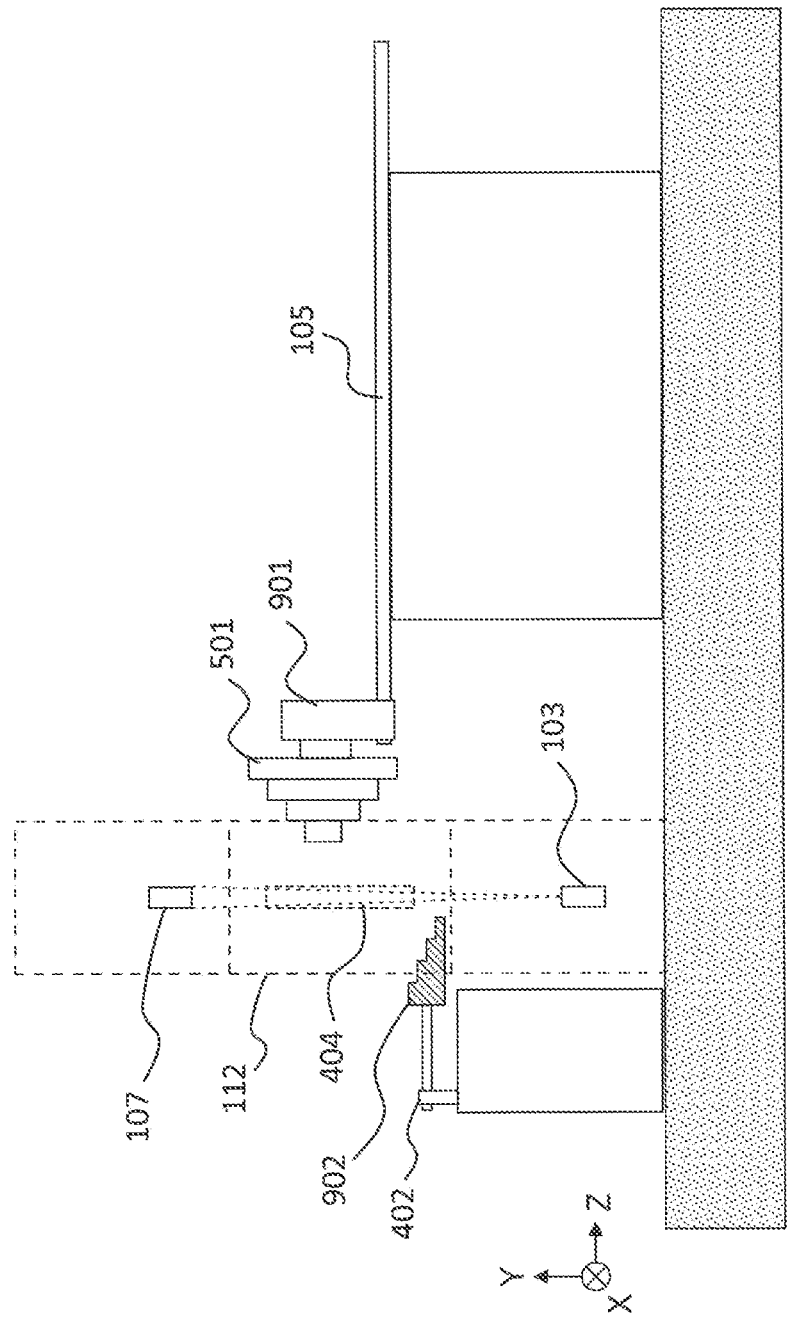
FIG. 9 is a diagram illustrating driving of the phantom.

With reference to FIG. 9, the driving of the phantom is described. In FIG. 9, the coupled elliptic phantom 501 formed of the first basis material 202 is mounted to the bad 105 through a support portion 901, and a second basis material phantom 902 formed on the second basis material 203 is mounted to the drive unit 402. Specifically, the coupled elliptic phantom 501 and the second basis material phantom 902 are individually moved into the opening 112 of the gantry 102 to be positioned within the radiation field 404 by the driving of the bed 105 and the driving of the drive unit 402, respectively. The individual movement of the coupled elliptic phantom 501 and the second basis material phantom 902 enables a reduction in movement distance in the Z axis direction as compared with the stepped phantom 301.

Figure 10:
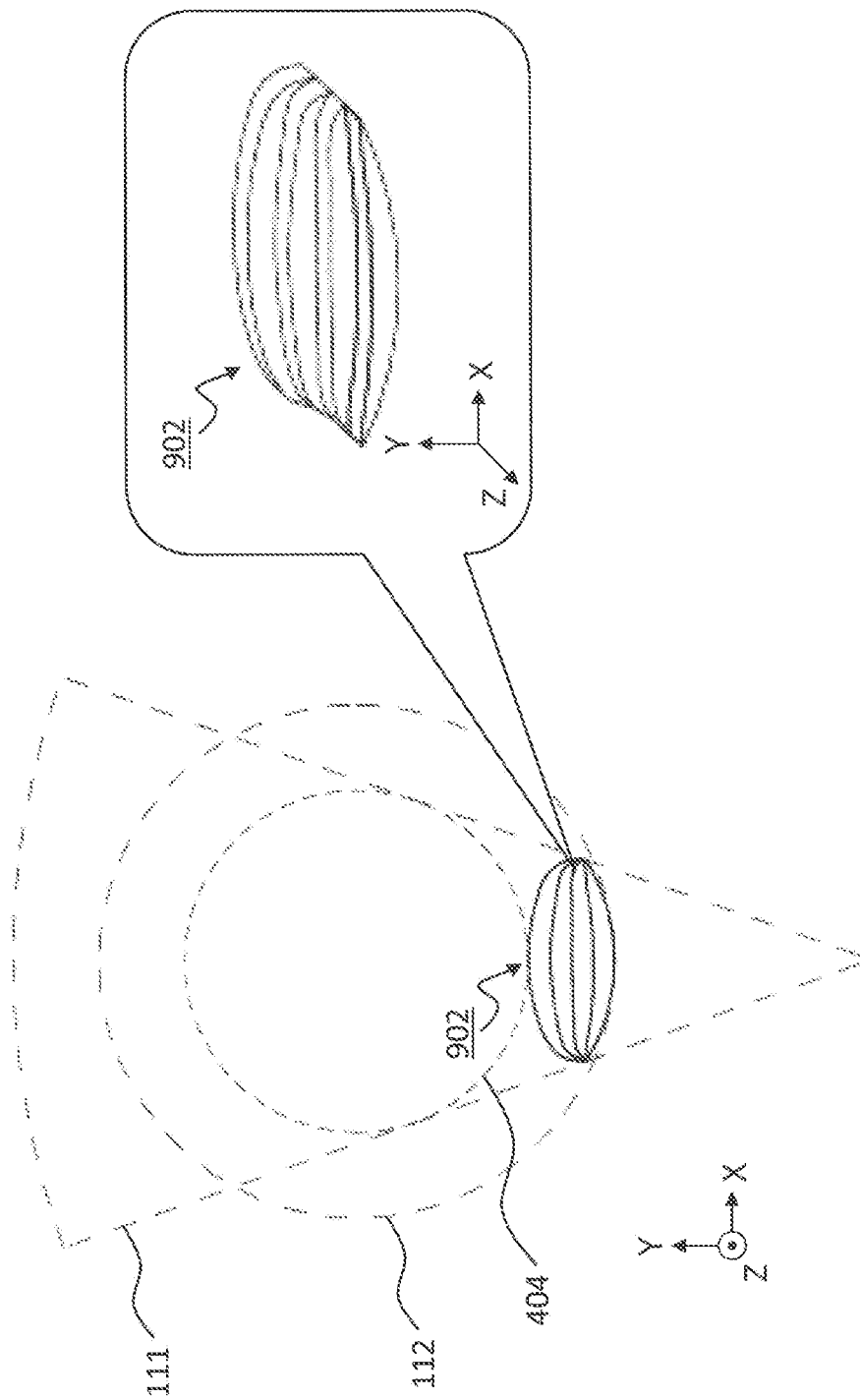
FIG. 10 is a diagram illustrating an example placement of a second basis material phantom.

With reference to FIG. 10, the placement of the second basis material phantom 902 is described. The second basis material 203 has a smaller X-ray attenuation coefficient than that of the first basis material 202, and therefore has a smaller thickness than the coupled elliptic phantom 501. It is noted that the second basis material phantom 902 may be in a shape of the coupled component phantom without a cylinder. If the second basis material phantom 902 is placed closer to the X-ray tube 103, a further reduction in size of the second basis material phantom 902 in the X-axis direction is enabled.

The examples of the phantom, the radiographic imaging device, and the method for calibrating a photon counting detector according to the present invention have been described. It is to be understood that the phantom, the radiographic imaging device, and the method for calibrating a photon counting detector according to the present invention are not limited to the above examples and may be embodied by modifying elements thereof without departing from the spirit or scope of the present invention. Further, a plurality of elements disclosed in the above examples may be combined as appropriate. Further, several elements of all the elements described in the above examples may be omitted.

REFERENCE SIGNS LIST

101 . . . X-ray CT apparatus
102 . . . gantry
103 . . . X-ray tube
104 . . . bowtie filter
105 . . . bed
106 . . . object under examination
107 . . . detector panel
108 . . . arithmetic apparatus
109 . . . input apparatus
110 . . . display apparatus
111 . . . X rays
112 . . . opening
201 . . . combination of basis materials
202 . . . first basis material
203 . . . second basis material
204 . . . calibration data
301 . . . stepped phantom
401 . . . carriage
402 . . . drive unit
404 . . . radiation field
501 . . . coupled elliptic phantom
701 . . . first component 702 . . . second component
703 . . . third component
710 . . . focal point
711 . . . contact point
712 . . . arc
901 . . . support portion
902 . . . second basis material phantom

What is claimed is:

1. A phantom used in acquisition of calibration data for a photon counting detector that outputs an electric signal based on photon energy of incident radiation,
the phantom comprising a first basis material,
wherein the first basis material varies in thickness in a stepwise fashion in a direction perpendicular to a radiation field of the radiation, and
wherein the phantom includes a plurality of elliptic cylinders stacked one on another, each cylinder comprising the first basis material, and the plurality of elliptic cylinders varying in length along a minor axis of each elliptic cylinder.

2. The phantom according to claim 1, wherein when N is the number of steps in the direction perpendicular to the radiation field, an i-th ellipse from one end of the direction perpendicular to the radiation field has a minor axis with a length that is i/N times a length of a major axis thereof.

3. The phantom according to 1, wherein the first basis material is moved in the direction perpendicular to the radiation field.

4. A radiographic imaging device, comprising:
a photon counting detector that outputs an electric signal based on photon energy of incident radiation; and
a storage for storing calibration data acquired using the phantom according to claim 1.

5. The phantom according to claim 1, wherein when N is the number of steps in the direction perpendicular to the radiation field, in an i-th step from one end of the direction perpendicular to the radiation field, a thickness of the first basis material in a direction in which the radiation passes through the first basis material is i/N times a length in which the radiation passes through the radiation filed.

6. The phantom according to claim 5, wherein a center of the thickness of the first basis material in the direction in which the radiation passes through the first basis material passes through a contact point between the radiation field and a tangent to the radiation field passing through a focal point of the radiation, and creates an arc that is centered around the focal point.

7. A phantom used in acquisition of calibration data for a photon counting detector that outputs an electric signal based on photon energy of incident radiation, the phantom comprising a first basis material,
wherein the first basis material varies in thickness in a stepwise fashion in a direction perpendicular to a radiation field of the radiation, and in each step, the step decreases in thickness with distance from a center of the radiation field in a direction of arrangement of detection elements of the photon counting detector, and
wherein when N is the number of steps in the direction perpendicular to the radiation field, in an i-th step from one end of the direction perpendicular to the radiation field, a thickness of the first basis material in a direction in which the radiation passes through the first basis material is i/N times a length in which the radiation passes through the radiation field.

8. The phantom according to claim 7, wherein a center of the thickness of the first basis material in the direction in which the radiation passes through the first basis material passes through a contact point between the radiation field and a tangent to the radiation field passing through a focal point of the radiation, and creates an arc that is centered around the focal point.

9. A method for calibrating a photon counting detector that outputs an electric signal based on photon energy of incident radiation, the method comprising the step of acquiring calibration data for the photon counting detector by using a phantom that includes a first basis material varying in thickness in a stepwise fashion in a direction perpendicular to a radiation field of the radiation and, in each step, the step decreasing in thickness with distance from a center of the radiation field in a direction of arrangement of detection elements of the photon counting detector,
when N is the number of steps in the direction perpendicular to the radiation field, in an i-th step from one end of the direction perpendicular to the radiation field, a thickness of the first basis material in a direction in which the radiation passes through the first basis material is i/N times a length in which the radiation passes through the radiation field.

10. The method according to claim 9, wherein a center of the thickness of the first basis material in the direction in which the radiation passes through the first basis material passes through a contact point between the radiation field and a tangent to the radiation field passing through a focal point of the radiation, and creates an arc that is centered around the focal point.

11. The method according to claim 9, further comprising:
moving the first basis material in the direction perpendicular to the radiation field.

12. The method according to claim 9, wherein
a cross section shape of the first basis material in the radiation field is an ellipse with a minor axis extending along radiation passing though the center of the radiation field,
the minor axis varies in length from one step to another in the direction perpendicular to the radiation field, and
the ellipse has a major axis equal in length in all steps in the direction perpendicular to the radiation field.

13. The method according to claim 12, wherein when N is the number of steps in the direction perpendicular to the radiation field, an i-th ellipse from one end of the direction perpendicular to the radiation field has a minor axis with a length that is i/N times a length of a major axis thereof.

* * * * *